United States Patent [19]

Karamian

[11] 4,276,256
[45] Jun. 30, 1981

[54] METHOD FOR PREVENTING BACTERIAL PASSAGE INTO STERILE FLUID SYSTEMS

[76] Inventor: Narbik A. Karamian, 7609 Exeter Rd., Bethesda, Md. 20014

[21] Appl. No.: 926,664

[22] Filed: Jul. 21, 1978

Related U.S. Application Data

[63] Continuation-in-part of Ser. No. 737,740, Nov. 1, 1976, abandoned.

[51] Int. Cl.³ .............................................. A61L 2/10
[52] U.S. Cl. .................................... 422/24; 137/241; 202/202; 250/432 R
[58] Field of Search ....................... 202/202; 137/241; 250/432 R; 422/24

[56] References Cited

U.S. PATENT DOCUMENTS

| | | | |
|---|---|---|---|
| 2,381,031 | 8/1945 | Blashfield | 137/241 |
| 2,537,774 | 1/1951 | Machinist | 210/64 X |
| 3,433,946 | 3/1969 | Hardwick | 250/432 R X |
| 3,589,862 | 6/1971 | Veloz | 250/432 X |

*Primary Examiner*—Frank W. Lutter
*Assistant Examiner*—Roger F. Phillips

[57] ABSTRACT

An apparatus for preventing microorganisms from passing from outside into sterile closed systems containing sterile water or fluids for general or biomedical use wherein an ultraviolet light source is attached to the outlet valve, exposing it to an effective amount of ultraviolet light of a wavelength range of 2300A° to 2900A°.

2 Claims, 8 Drawing Figures

METHOD FOR PREVENTING BACTERIAL PASSAGE INTO STERILE FLUID SYSTEMS

CROSS REFERENCE TO OTHER APPLICATIONS

This application is a continuation in part of application Ser. No. 737,740 filed Nov. 1, 1976, and now abandoned.

FIELD OF THE INVENTION

The invention relates to an apparatus for preventing microorganism contamination from outside environment into water or other fluids that have been previously sterilized to assure that they are microorganism free. The fluid drawn off through this apparatus either continuously or intermittently will remain microorganism free even after substantial outside surface bacterial contamination of the apparatus. This contamination may arise from handling and/or from environmental factors.

BACKGROUND OF THE INVENTION

There has been a constant demand for high purity bacteria and endotoxin free water for research and intravenous admixtures. My co-pending application Ser. No. 671,713 filed Mar. 29, 1976, now U.S. Pat. No. 4,089,749 describes an apparatus for preparing such water. The references cited in this application disclose prior art systems for preparing high purity bacteria and endotoxin free water.

Very briefly this application describes an apparatus for the continuous production of high-purity water including a distillation flask, a carboy and a condenser unit. A filter is provided between the atmosphere and the interiors of the flask, the carboy and the condenser unit to remove airborne bacteria from entering the flask. The open parts are interconnected with flexible tubing. A two-way stopcock allows high-purity water to be removed from the carboy.

It has been found that although the apparatus for producing high-purity water described in application Ser. No. 671,713 produces a high quality product, there is a possibility of bacterial contamination of the product being stored in the system from outside through the ordinary two way faucet being used for drawing off water. The bacteria, generally are either airborne or grow on human skin and transfer on to the valve during handling.

Various devices have been proposed for preparing sterile liquids. U.S. Pat. No. 2,456,152 describes a device wherein the outlet faucet is continuously bathed in steam. U.S. Pat. No. 2,537,774 relates to a device that utilizes ultraviolet radiation to sterilize liquids. French Pat. No. 1,101,643 uses a combination of ultraviolet and infrared radiation to prepare sterile liquids.

In all of these devices either the liquid being withdrawn is heated to a temperature substantially above room temperature, or there is no provision for preventing bacterial contamination from outside sources.

SUMMARY OF THE INVENTION

It is the principal object of the invention to provide an apparatus for preventing bacterial contamination of water or other liquids that have been previously treated to assure that they are sterile without increasing the temperature of the liquid being withdrawn.

It is another object of the present invention to provide a continuous source of high purity, bacteria free water or other fluids by assuring that sources of this water or fluids are not recontaminated through bacterial accumulation on the valves or faucets connected to the system.

DETAILED DESCRIPTION OF THE PREFERRED EMBODIMENT

Ultraviolet radiation of wavelength range between 2300 A and 2900 A. is particularly destructive to all forms of germ life, especially those organisms found in water and for this reason such a radiator is ideal for a means of sterilization.

Figures 1, 2:
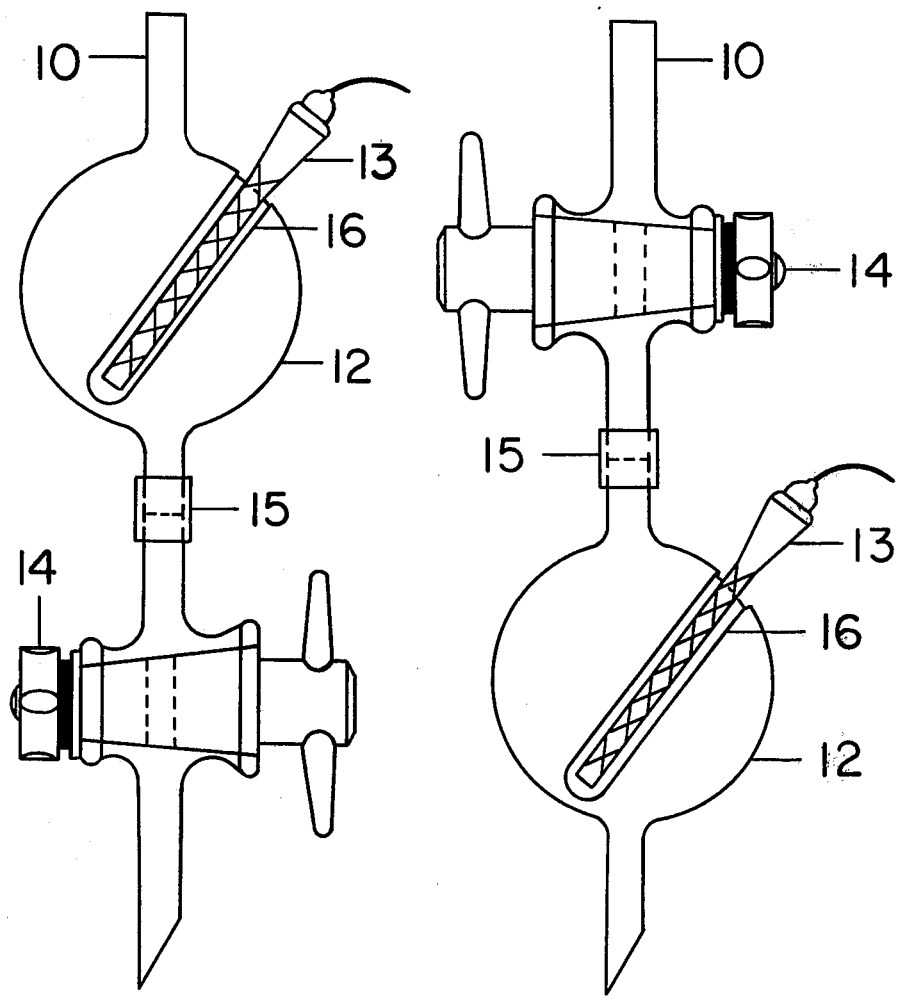
FIG. 1 is a pictorial partly schematic diagram of one embodiment of the invention.
FIG. 2 is another partially schematic diagram of an apparatus for preventing recontamination of the water.

Referring now to FIG. 1. The water or fluids to be protected is stored in a suitable vessel, not shown, having an oulet means for withdrawing fluid from the vessel comprising apparatus 12, having connecting tubing 10, and stopcock 14 connected with apparatus 12 by means of Teflon tubing 15 or by any other means. The essential feature of this apparatus is the provision of a source of ultraviolet radiation 13 attached at the apparatus 12 that connects the supply vessel to the stopcock 14. FIG. 2 shows another embodiment of the device wherein the apparatus 12 containing the ultraviolet source is connected below the stopcock 14.

Figures 3, 4:
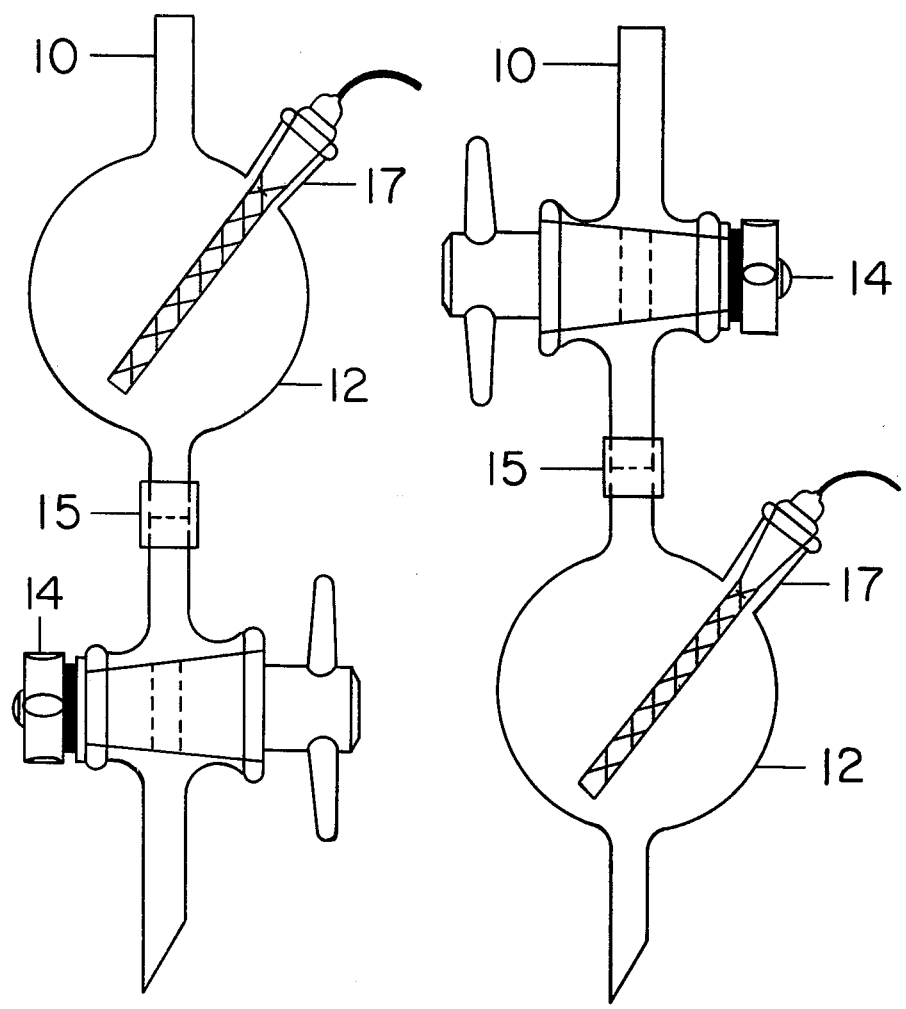
FIGS. 3 thru 8 show other embodiments of the device.
Figures 5, 6:
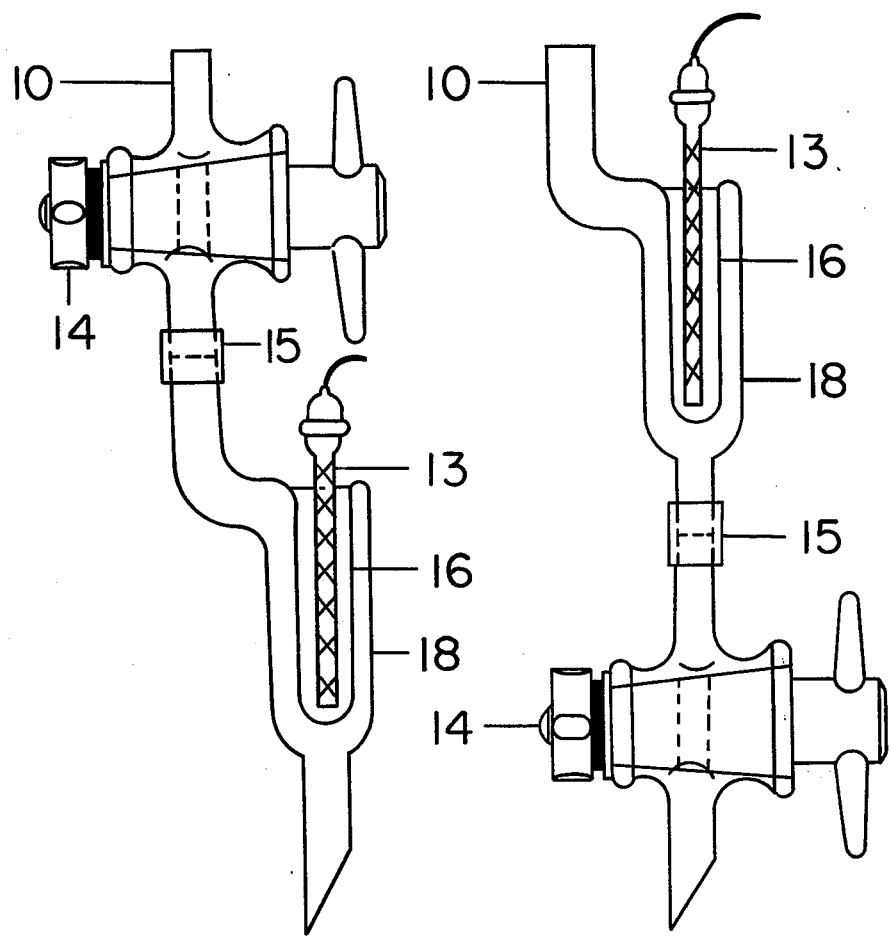
Figures 7, 8:
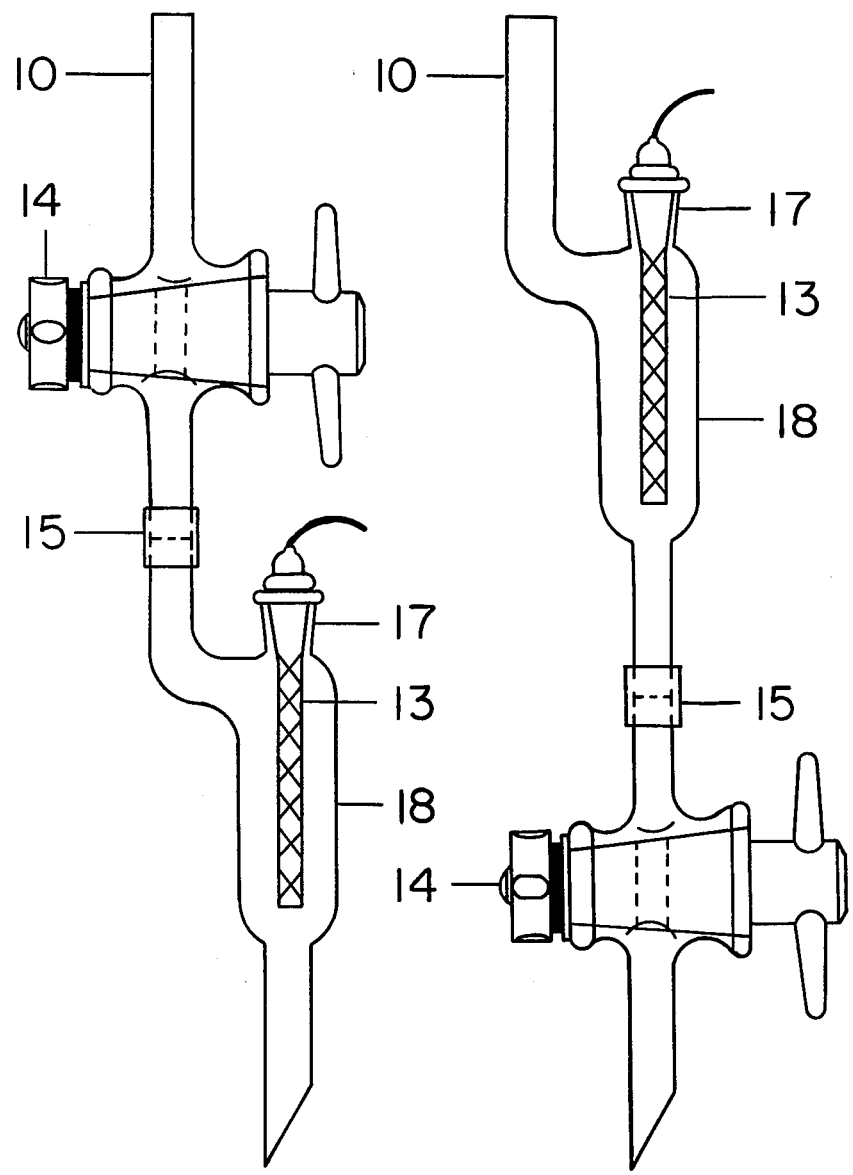

In FIGS. 1 and 2 the ultraviolet source is contained in a tube 16. FIGS. 3 and 4 disclose other embodiments of the invention in which the ultra violet source is mounted in the apparatus 12 without use of a protective envelope 16. In these embodiments the ultraviolet source is mounted in a ground glass joint 17 attached to apparatus 12. FIGS. 5 and 6 show another embodiment of the invention in which the apparatus is modified by provision of a U-shaped structure 18 in which the ultraviolet source is mounted. The embodiment shown in FIG. 5 is similar to the embodiment shown in FIG. 1 in that the U-shaped structure 18 is positioned above the stopcock 14. FIG. 6 shows a structure similar to the structure of FIG. 2 in that ultraviolet light source 13 is positioned in the U-shaped structure 18 below the stopcock 14. FIG. 7 shows another embodiment of the invention in which the ultraviolet source 13 is positioned in the U-shaped structure 18 by means of a joint 17 in the apparatus where the unit 13 is positioned above the stopcock 14. FIG. 8 illustrates another embodiment wherein the U-shaped member, 18 with the ultraviolet light source 13 is contained in a joint 17 is positioned below the stopcock 14.

It is essential that the apparatus 12, 18 be made of quartz to assure that the ultraviolet llight is penetratable into the liquid surrounding the light. However, in the apparatus shown in FIGS. 3 and 4 and FIGS. 7 and 8 only the envelope of the ultraviolet light source 13 is necessarily made of quartz.

In operation the apparatus 12 is connected by means of the tube 10 to the source of the supply of the bacteria free water and the ultraviolet source is turned on and off intermittently. When the apparatus is not in use, the water in the reservoir cannot become contaminated by bacteria thru the stopcock because bacteria cannot grow and move toward the water reservoir. The ultraviolet light 13 prevents this movement. The inclusion of the apparatus 12 in the system provides a means of assuring that the stopcock 14 is kept free of contamination, and thus avoids the elaborate precaution such as sterilizing the exterior of the stopcock, etc., as described in the application Ser. No. 671,713.

The essential feature of the system is the maintenance of the effluent liquid from the system free of bacterial contamination without an attendant increase in temperature. The liquid is subjected to ultraviolet radiation intermittently. The light is on for 10 to 45 seconds at 1 to 3 hour intervals. Thus the liquid is not exposed to ultraviolet radiation for periods of time that are long enough to increase the temperature. Selection of a specific exposure time between 10 and 45 seconds depends upon the type of microorganisms being controlled.

The apparatus is a separate unit of small size that can be easily removed and replaced if necessary. The small size of the apparatus also precludes generation of enough heat to increase the temperature of the fluid being withdrawn.

The apparatus is a self contained unit that ca be adapted for use in any system where it is necessary or desirable to prevent bacterial contamination from an outside source.

Although my invention is described with reference to the apparatus disclosed in Ser. No. 617,713, it is obvious that it is equally applicable to other systems for protecting a source of bacteria free fluid from bacterial contamination.

My invention is illustrated by the following specific but non-limiting example:

EXAMPLE

A quantity of high-purity distilled water was prepared using the system disclosed in my co-pending application Ser. No. 617,713. The water was found to be free of bacteria. The exterior of the stopcock was intentionally contaminated with bacteria. A few days later the water in the reservoir was found to be contaminated by several strains of bacteria that entered from the stopcock surface into the reservoir. The system was drained, sterilized and the run repeated after the apparatus shown in FIGS. 1 thru 8 was attached. The water in the reservoir remained bacteria free.

Although in my invention as described, an ultraviolet light source is positioned in the apparatus 12 as shown in FIGS. 3 and 4 and in the U-shaped structure shown in FIGS. 7 and 8; it is obvious that other modifications will give satisfactory results. The ultraviolet light sources shown in FIGS. 3, 4 7 and 8 can be replaced by silver rods. Alternatively the interior surfaces of the apparatus 12 and the U-shaped structure 18 can be coated with metalic silver. Ozone may also be used to assure the liquid is not contaminated by bacteria from an outside source.

What is claimed is:

1. A method of preventing microorganism contamination of a supply of sterile fluid stored in a reservoir, said reservoir comprising a vessel and outlet means for withdrawing fluid from said vessel, said outlet means comprising a quartz apparatus, by attaching an ultraviolet light source having a wavelength range of 2300 A° to 2900 A° at said quartz apparatus and intermittently exposing said quartz apparatus to an effective amount of ultraviolet light emitted from said light source, the exposure intervals being of such duration that said stored fluid is maintained at substantially room temperature.

2. The method according to claim 1 wherein said outlet means further comprises a valve and said apparatus and ultraviolet light source are positioned below said valve.

* * * * *